(12) United States Patent
McCabe

(10) Patent No.: US 6,172,114 B1
(45) Date of Patent: Jan. 9, 2001

(54) CREATINE SUPPLEMENT

(75) Inventor: David J. McCabe, Largo, FL (US)

(73) Assignee: Worldwide Sports Nutritional Supplements, Inc., Largo, FL (US)

( * ) Notice: Under 35 U.S.C. 154(b), the term of this patent shall be extended for 0 days.

(21) Appl. No.: 09/408,743

(22) Filed: Sep. 30, 1999

(51) Int. Cl.⁷ .................. A61K 31/195; A61K 31/70
(52) U.S. Cl. ................................ 514/565; 514/23
(58) Field of Search ................ 514/565, 25, 479

(56) References Cited

U.S. PATENT DOCUMENTS

| | | | |
|---|---|---|---|
| 4,582,807 | * 4/1986 | Veeraraghavan | 435/32 |
| 5,397,786 | * 3/1995 | Simone | 514/300 |
| 5,612,375 | * 3/1997 | Sueoka | 514/565 |
| 5,908,864 | * 6/1999 | Casey | 514/564 |

* cited by examiner

*Primary Examiner*—William R. A. Jarvis
*Assistant Examiner*—Vickie Kim
(74) *Attorney, Agent, or Firm*—Heslin & Rothenberg, P.C.; Leo M. Loughlin, Esq.

(57) ABSTRACT

A creatine supplement comprising creatine and ribose in a pharmaceutically acceptable vehicle for internal administration. The supplement further includes nutrients selected from the group consisting of vitamins, minerals, amino acids and liquid carbohydrates. In addition, the supplement includes a suitable pharmaceutical excipient selected from the group consisting of fillers, lubricants, binders, colorings and flavorings. Further, the supplement is in a pharmaceutical carrier selected from the group consisting of a tablet, capsule, cream, ointment, solution, gel, suspension, suppository or spray. Finally, the creatine in said supplement is creatine monohydrate

13 Claims, No Drawings

CREATINE SUPPLEMENT

FIELD OF THE INVENTION

The present invention relates to a supplement which contains a combination of creatine and ribose.

BACKGROUND OF THE INVENTION

The present invention relates to method and means of forming a dietary supplement comprising creatine and ribose. Creatine is a nitrogenous acid widely distributed in the muscular tissue of the body. It has the chemical name N-methyl-N-guanylglycine. Creatine is synthesized in the body through the processing of the amino acids glycine, arginine, and methionine.

ATP is the immediate source of energy for muscle contraction. However, the amount of ATP in muscle is small. Therefore, a reserve supply of readily available energy is needed. Creatine in muscle serves as a reservoir of high-potential phosphoryl groups. Creatine catalyzes the reversible transfer of a phosphoryl group from creatine phosphate to ADP to form ATP.

Creatine is available from many food sources and can be found in the muscle of most mammals and fish, including beef, chicken, cod, herring, pork, salmon, tuna and turkey. Since most of the high creatine-containing food are also high in fat and cholesterol, creatine supplements have become a popular source of obtaining the nutrient. Creatine monohydrate is the preferred form of creatine available since it is tasteless and odorless white powder which is combined with liquid prior to consumption.

The body-building industry has widely promoted the benefits of creatine supplements as a means of increasing body mass, strength and energy for reducing body fat. Once creatine enters the muscle fibers, it accumulates and stays there for several weeks. Thus, the strategy behind creatine supplements is to fill the muscles with the nutrient to capacity and then to take only an amount sufficient to keep the creatine stores full. The creatine dose is estimated from the total creatine storage capacity in a person's body, which is directly related to the person's muscle mass, as well as the person's weight and level of exercise. However, creatine use is associated with certain side effects such as diarrhea and nausea. Accordingly, it is a primary objective of the present invention to prepare an effective supplement which is useful for increasing muscle strength, power and mass without the unwanted side effects of previous creatine supplements.

SUMMARY OF THE INVENTION

The present invention relates to a method and means for increasing muscle strength, power and mass, with a supplement comprising creatine and ribose. The supplement of the present invention is an improvement over the creatine supplements of the prior art.

DETAILED DESCRIPTION OF THE INVENTION

The present invention relates to a new creatine supplement comprising creatine and ribose.

This invention is predicated upon the discovery that creatine combined with ribose can be formulated into a supplement which has all the benefits of creatine supplements without exhibiting serious side effects. The major ingredients of the supplement according to the present invention are creatine and ribose. The amount of creatine to ribose and/or the amount of creatine to ribose and minors in the composition is variable, but is preferred to be in the any range from about 50% to 99% creatine, more preferably about 85% to 99%, and even more preferably about 95% to 99%. However, the dosage for creatine in the supplement may be about 2 to 6 grams, with the amount of ribose therein between about 100 milligrams to 3 grams. Thus, the ratio of creatine to ribose may be as low as almost 2:3, and as high as about 6:1.

The other major ingredient of the supplement is ribose. It is preferred that the creatine be creatine monohydrate. Both creatine monohydrate and ribose are commercially available.

It is also contemplated that certain minors can be added to the composition. It should be understood that the term "minors" is not being used from the standpoint of their effect on the composition, but merely from the standpoint of a characterization of the amount that is present in comparison with the higher weight percent levels of creatine and ribose. Such minors include excipients such as dyes, flavorings, lubricants, binders, fillers, vitamins, minerals and amino acids.

There is no particular order or method that is used to prepare the creatine supplement. The only requirement is that the ingredients be combined homogeneously. The preferred method involves the use of a high-speed mixing and high-speed shearing device to combine the ingredients more efficiently and completely. If the liquid carbohydrates are included in the supplement, it is preferred that the liquid carbohydrates be combined first with the ribose since these ingredients are more compatible. The creatine is then added.

The temperature during the mixing of the ingredients may not be important. Satisfactory results are obtained at room temperature.

While creatine is conventionally supplemented in a loose powder form, it is also contemplated that it can be contained in a variety of other dosage forms. In general, in addition to the active compounds, creatine and ribose, the pharmaceutical compositions of this invention may contain suitable ingredients which facilitate processing of the active compounds into preparations which can be used pharmaceutically. Dosage forms encompass tablets, capsules, cream, ointment, solution, gel, suppository and spray.

The pharmaceutical preparations of the present invention are manufactured in a manner well known in the art. Pharmaceutical preparations are typically made by means of conventional mixing, granulating or dissolving. The processes to be used will depend ultimately on the physical properties of the active ingredients used. Suitable ingredients to facilitate processing of the active compounds are fillers such as sugars, for example, lactose. If desired, disintegrating agents may used such as starch.

Other pharmaceutical preparations which can be used orally include push-fit capsules made of gelatin, as well as soft, sealed capsules made of gelatin and a plasticizer such a glycerol or sorbitol. The push-fit capsules can contain the active compounds in a form of granules which may be mixed with fillers such as lactose, binders such a starches, and/or lubricants such as talc or magnesium stearate and, optionally, stabilizers. In soft capsules, the creatine and ribose are preferably dissolved or suspended in suitable liquids, such as fatty oil or liquid paraffin.

It is believed that the creatine supplement of the present invention is an improvement over supplements of the prior art. Creatine mixed with ribose creates a supplement with all the benefits of creatine and may have fewer side effects.

While the present invention has been shown in certain embodiments, it is contemplated that minor modifications of the composition and ranges expressed herein may made and still come within the scope and spirit of the present invention.

What is claimed is:

1. A creatine supplement comprising:

creatine; and ribose;

said creatine and ribose in a pharmaceutically acceptable vehicle for a tablet or capsule.

2. A supplement according to claim 1 wherein the supplement further includes nutrients selected from the group consisting of vitamins, minerals, amino acids and liquid carbohydrates.

3. A supplement according to claim 1 wherein the supplement further includes a suitable pharmaceutical excipient selected from the group consisting of fillers, lubricants, binders, colorings and flavorings.

4. A supplement according to claim 1 wherein said creatine is creatine monohydrate.

5. A method of preparing a creatine supplement consisting essentially of:

mixing creatine with ribose; and placing the creatine and ribose in pharmaceutically acceptable vehicle for a tablet or capsule.

6. A method according to claim 5 wherein the creatine and ribose are homogeneously mixed.

7. A method according to claim 5 including the addition of ingredients selected from the group consisting of vitamins, minerals, amino acids and liquid carbohydrates.

8. A method according to claim 5 wherein the creatine and ribose are combined with a high-shear mixer.

9. A method according to claim 5 wherein said creatine is creatine mono hydrate.

10. A method of preparing a creatine supplement comprising:

combining a supplement amount of creatine with ribose and additional ingredients selected from a group consisting of vitamins, minerals, amino acids and liquid carbohydrates;

wherein the liquid carbohydrate and ribose are combined first to form a mixture, and the creatine is combined with the mixture thereafter; and placing said supplement amount of creatine, ribose, and additional ingredient in a suitable pharmaceutical carrier for a tablet or capsule.

11. A method according to claim 10 wherein said creatine is creatine monohydrate.

12. A method of increasing muscle mass and strength comprising:

ingesting a supplement comprising creatine and ribose wherein said supplement is in a pharmaceutical carrier suitable for a tablet or capsule.

13. A method according to claim 12 wherein said creatine is creatine monohydrate.

* * * * *